US008612258B2

(12) United States Patent
Moitra et al.

(10) Patent No.: US 8,612,258 B2
(45) Date of Patent: Dec. 17, 2013

(54) METHODS AND SYSTEM TO MANAGE PATIENT INFORMATION

(75) Inventors: Dipen Moitra, Scotia, NY (US); Saurav Mullick, West Bengal (IN); Parmendra Tyagi, Uttar Pradesh (IN); Sreedhanya Gn, Karnataka (IN)

(73) Assignee: General Electric Company, Schenectady, NY (US)

( * ) Notice: Subject to any disclaimer, the term of this patent is extended or adjusted under 35 U.S.C. 154(b) by 306 days.

(21) Appl. No.: 12/263,252

(22) Filed: Oct. 31, 2008

(65) Prior Publication Data

US 2010/0114588 A1 May 6, 2010

(51) Int. Cl.
*G06Q 50/00* (2012.01)
*G06Q 10/00* (2012.01)

(52) U.S. Cl.
USPC .................................. 705/3; 705/2

(58) Field of Classification Search
USPC ......................................... 705/2–3
See application file for complete search history.

(56) References Cited

U.S. PATENT DOCUMENTS

| | | | | |
|---|---|---|---|---|
| 5,592,374 A | * | 1/1997 | Fellegara et al. | 705/3 |
| 5,664,109 A | * | 9/1997 | Johnson et al. | 705/2 |
| 6,826,536 B1 | * | 11/2004 | Forman | 705/4 |
| 6,912,549 B2 | | 6/2005 | Rotter et al. | |
| 2002/0111826 A1 | * | 8/2002 | Potter et al. | 705/2 |
| 2004/0153345 A1 | * | 8/2004 | Heckle | 705/3 |

OTHER PUBLICATIONS

Bui, TimeLine: Visualizing Integrated Patient Records, 2007, Information Technology in Biomedicine, IEEE Transactions on, vol. 11, No. 4, pp. 462,473.*
"Master Patient Index (MPI) Project Oasis Data Cleansing and Patient Matching Proposal," Worcestershire Health ICT Programme, Oct. 17, 2005 (17 pages).
"Sun Elndex Single Patient Identifier," Enterprise Master Patient Index, 2006 Sun Microsystems, Inc. (2 pages).

* cited by examiner

*Primary Examiner* — Tran Nguyen
(74) *Attorney, Agent, or Firm* — Hanley, Flight and Zimmerman, LLC

(57) ABSTRACT

Methods and system to manage patient information are described. An example computer-implemented method to manage patient information includes analyzing a first patient identification to extract first information. Additionally, the example method includes comparing the extracted first information to extracted second information related to a second patient identification to determine if the first patient identification and the second patient identification are associated with the same patient. Further, the example method includes associating the first information and the second information with the same patient identification when the first patient identification and the second patient identification are determined to be associated with the same patient.

22 Claims, 12 Drawing Sheets

METHODS AND SYSTEM TO MANAGE PATIENT INFORMATION

BACKGROUND

Healthcare environments, such as hospitals and clinics, typically include information systems (e.g., hospital information systems (HIS), radiology information systems (RIS), storage systems, picture archiving and communication systems (PACS), electronic medical records (EMR), etc.) to manage clinical information, management information, financial information, and/or scheduling information. The information may be centrally stored or divided into a plurality of locations. Healthcare practitioners may desire to access patient information at various points in a healthcare workflow. For example, during an encounter with a patient, medical personnel may access patient information, such as a patient's medical history and/or a patient's symptoms in an ongoing medical procedure. Alternatively, medical personnel may enter new information, such as history, diagnostic, or treatment information, into a medical information system during an ongoing medical procedure.

Medical practitioners, such as doctors, surgeons, and other medical professionals, rely on clinical information stored in such systems during an encounter(s) with a patient to, for example, assess the condition of a patient, provide immediate treatment in an emergency situation, diagnose a patient and/or provide any other medical treatment or attention. Additionally, medical administrators rely on financial information stored in such systems to generate medical bills associated with the encounter(s) with the medical practitioners and/or the medical personnel. As a result, if the clinical information, the financial information and/or any other information related to an encounter(s) between a patient and medical personnel stored on such systems is inaccurate and/or incomplete, managing a quality of delivered care provided to a patient and/or generating accurate medical bills associated with the encounter(s) may be compromised.

SUMMARY

In accordance with a disclosed example, an example computer-implemented method to manage patient information includes analyzing a first patient identification to extract first information. Additionally, the example method includes comparing the extracted first information to extracted second information related to a second patient identification to determine if the first patient identification and the second patient identification are associated with the same patient. Further, the example method includes associating the first information and the second information with the same patient identification when the first patient identification and the second patient identification are determined to be associated with the same patient.

In accordance with another disclosed example, a medical information system includes a data store in communication with one or more data entry systems to receive and store medical reports in the data store transmitted from the one or more data entry systems. Additionally, the example medical information system includes a report analyzer to extract data associated with at least one of patient identifications or patient encounter identifications. Further, the example medical information system includes a comparator to compare the extracted data to determine if the patient identifications are associated with the same patient. Further still, the example medical information system includes a record merger to at least associate different patient identifications with the same patient identification when the respective patient identifications that are associated with the same patient.

Figure 1A:
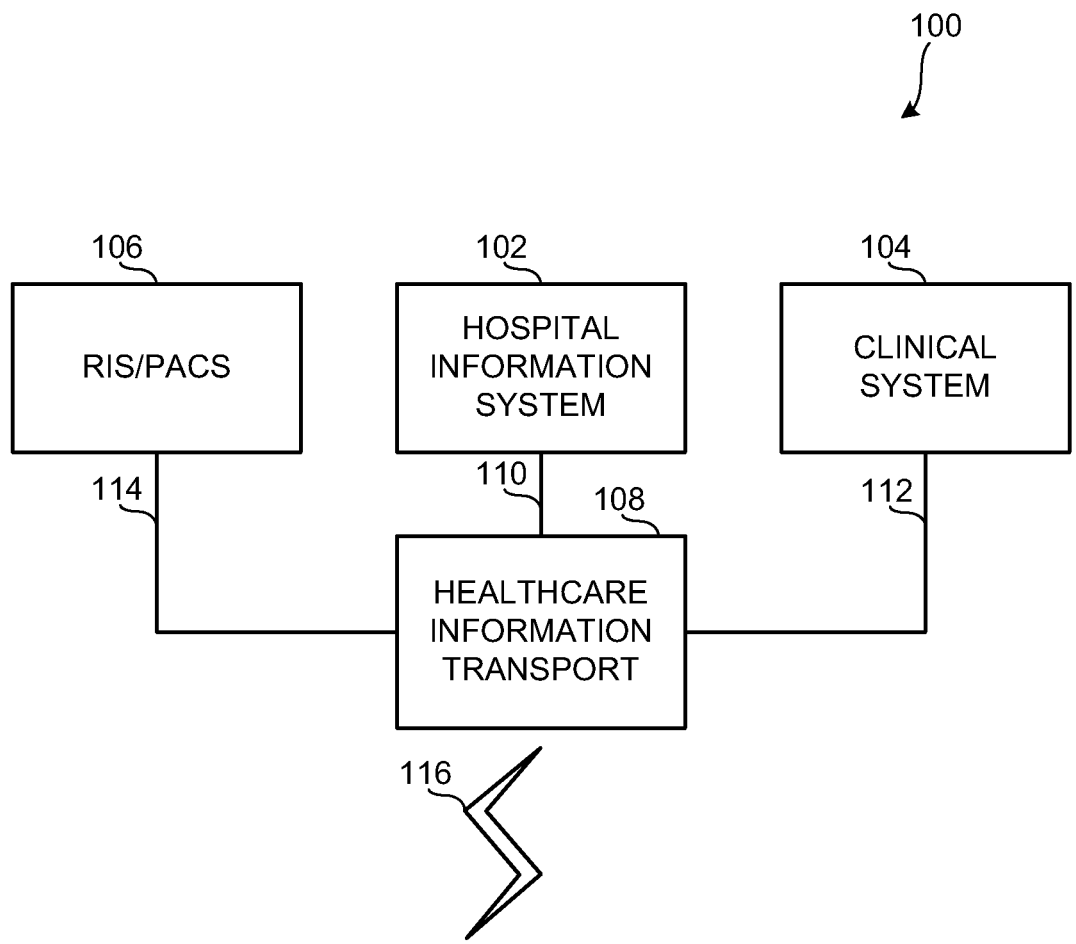
FIG. 1A is a block diagram of example clinical architecture used to implement an example medical information system.

The foregoing summary, as well as the following detailed description of certain example implementations, will be better understood when read in conjunction with the appended drawings. For the purpose of illustrating the example methods and systems described herein, certain implementations are shown in the drawings. It should be understood, however, that the example methods and systems are not limited to the arrangements and instrumentality shown in the attached drawings.

DETAILED DESCRIPTION

Although the following discloses example methods, apparatus, systems, and articles of manufacture including, among other components, firmware and/or software executed on hardware, it should be noted that such methods, apparatus, systems and articles of manufacture are merely illustrative and should not be considered as limiting. For example, it is contemplated that any or all of these firmware, hardware, and/or software components could be embodied exclusively in hardware, exclusively in software, exclusively in firmware, or in any combination of hardware, software, and/or firmware. Accordingly, while the following describes example methods, apparatus, systems, and/or articles of manufacture, the examples provided are not the only way(s) to implement such methods, apparatus, systems, and/or articles of manufacture. The example methods and apparatus described herein may be practiced in distributed computing environments where tasks are performed by local and remote processing devices that are linked (either by hardwired links, wireless links, or by a combination of hardwired or wireless links) through a communications network.

The example methods and systems described herein manage and merge patient information associated with encounters to advantageously enable healthcare practitioners to more quickly and efficiently review and/or organize patient information related to a patient encounter to a patient medical record and/or history. In particular, the example methods and systems described herein identifies and automatically merges associated encounters into medical records and/or histories associated with a particular patient, which thereafter can be advantageously utilized in clinical decision support. In addition, the example methods and systems described herein decrease the likelihood that critical information is missed or mistakenly overlooked during a patient encounter and, thus, the quality of delivered patient care is increased. Further, the example methods and systems described herein enable healthcare practitioners to accurately audit and/or monitor the quality of provided care to ensure compliance with clinical guidelines. Further still, the example methods and systems described herein ensure accuracy associated with financial statements and compliance with reimbursement procedures while minimizing the number of billing disputes.

FIG. 1A is a block diagram of example clinical architecture 100 used to implement an example medical information system capable of implementing the example methods and apparatus described herein to manage patient information associated with patient encounters. The example clinical architecture 100 includes a hospital information system 102, a clinical system 104, a radiology information system (RIS)/a picture archiving and communication system (PACS) 106 and a healthcare information transport 108. The hospital information system 102, the clinical system 104, the RIS/PACS 106 and the healthcare information transport 108 may be linked (either by hardwired links, wireless links, or by a combination of hardwired or wireless links) through a communications network. In the illustrated example, clinical information architecture may include the hospital information system 102, the clinical system 104, the RIS/PACS 106 and the healthcare information transport 108, which are housed in a healthcare facility and locally archived. However, in other implementations, the hospital information system 102, the clinical system 104, the RIS/PACS 106, and/or the healthcare information transport 108 may be housed in one or more other suitable locations. Furthermore, one or more components of the clinical architecture 100 may be combined and/or implemented together. For example, the clinical system 104 and/or the RIS/PACS 106 may be integrated with the hospital information system 102; the RIS/PACS 106 may be integrated with the clinical system 104; and/or the three example information systems 102, 104, and/or 106 may be integrated together. In other example implementations, the clinical architecture 100 includes a subset of the illustrated information systems 102, 104, and/or 106. For example, the clinical architecture 100 may include only one or two of the hospital information system 102, the clinical system 104, and/or the RIS/PACS 106. Preferably, information (e.g., test results, observations, diagnosis, etc.) is entered into the hospital information system 102, the clinical system 104, and/or the RIS/PACS 106 by healthcare practitioners (e.g., radiologists, physicians, and/or technicians) before, during and/or after a patient examination and/or encounter.

The hospital information system 102 stores medical information such as clinical reports, patient information, and/or administrative information received from, for example, personnel at a hospital, clinic, and/or a physician's office. The clinical system 104 may include one or more of, for example, an outpatient care system, a prenatal system, an inpatient system and/or a preoperative system, each of which may store information such as, for example, messages, warnings, alerts, patient scheduling information, patient demographic data, patient tracking information, and/or physician and patient status monitors.

The RIS/PACS 106 stores medical images (e.g., x-rays, scans, three-dimensional renderings, etc.) such as, for example, digital images in a database or registry. In some examples, the medical images are stored in the RIS/PACS 106 using the Digital Imaging and Communications in Medicine (DICOM) format. Images are stored in the RIS/PACS 106 by healthcare practitioners (e.g., imaging technicians, physicians, radiologists, etc.) after a medical imaging of a patient and/or are automatically transmitted from medical imaging devices to the RIS/PACS 106 for storage. In some examples, the RIS/PACS 106 may also include a display device and/or viewing workstation to enable a healthcare practitioner to communicate with the RIS/PACS 106. Additionally, the RIS/PACS 106 enables exam order entry (e.g., ordering an x-ray of a patient) and image and film tracking (e.g., tracking identities of one or more people that have checked out a film). In some examples, information in the RIS/PACS 106 is formatted according to the HL-7 (Health Level Seven) clinical communication protocol. While FIG. 1A depicts the RIS/PACS 106 as implemented together, in other examples, the RIS and the PACS may be implemented separately.

Figure 1B:
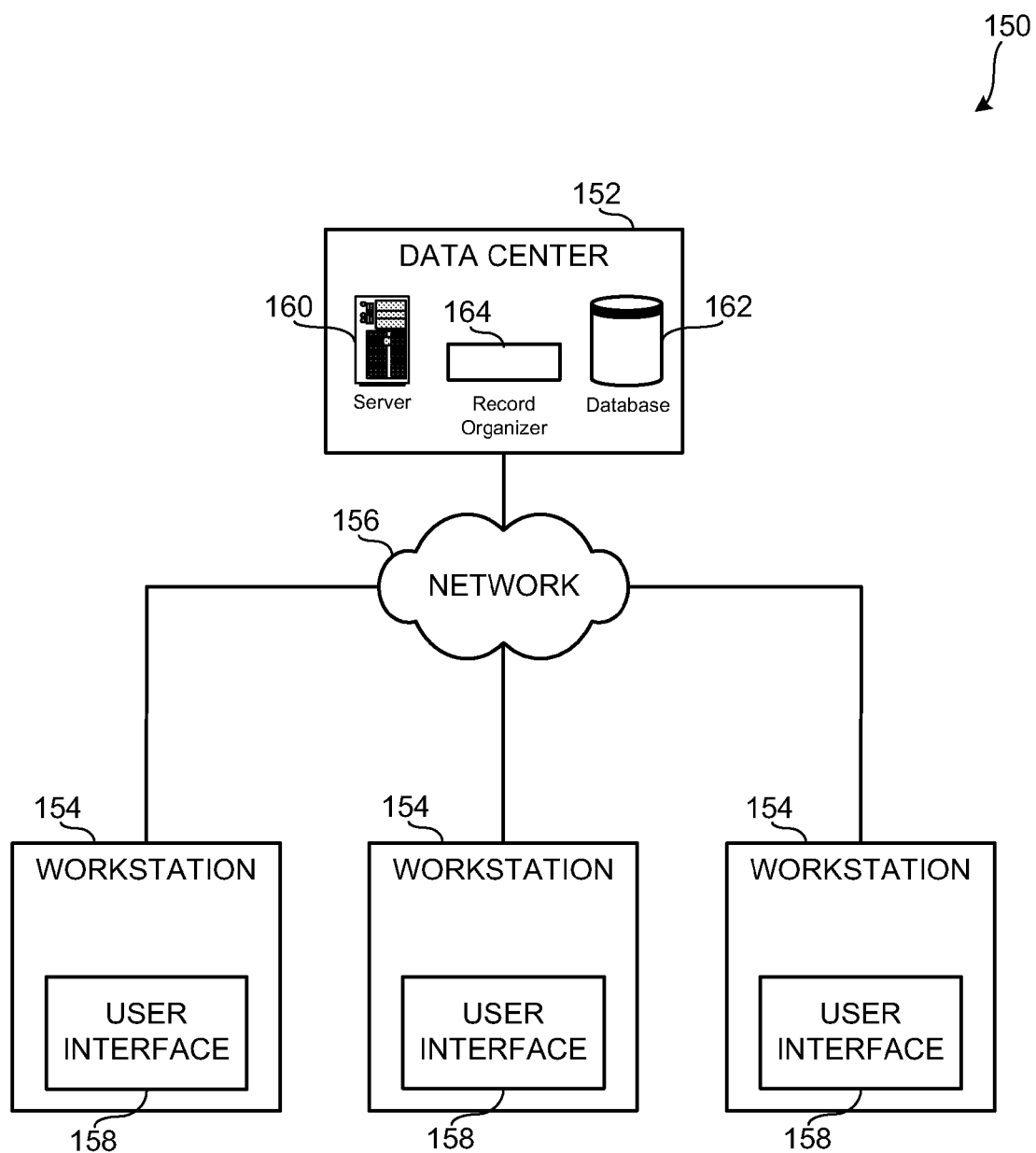
FIG. 1B is a block diagram of example system architecture used to implement the example medical information system.

The healthcare information transport 108 includes a hospital information system interface connection 110, a clinical system interface connection 112, a RIS/PACS interface connection 114, and a data center interface connection 116. The healthcare information transport 108 facilitates communication among the hospital information system 102, the clinical system 104, the RIS/PACS 106, and/or a data center 152 (FIG. 1B). The interface connections 110, 112, 114, and 116 may be implemented by, for example, a Wide Area Network (WAN) such as a private network or the Internet or a Local Area Network (LAN). Accordingly, the healthcare information transport 108 includes one or more communication components such as, for example, an Ethernet device, an asynchronous transfer mode (ATM) device, an 802.11 device, a DSL modem, a cable modem, a cellular modem, etc.

FIG. 1B is a block diagram of example system architecture 150 used to implement the example medical information system. The example system architecture 150 includes the data center 152 and a plurality of workstations 154. The data center 152, and the plurality of workstations 154 may be linked (either by hardwired links, wireless links, or by a combination of hardwired or wireless links) through a communications network. The data center 152 communicates with the plurality of workstations 154 via a network 156, implemented at a plurality of locations (e.g., a hospital, clinic, doctor's office, other medical office, or terminal, etc.). The network 156 is implemented by, for example, the Internet, an intranet, a private network, a wired or wireless Local Area Network, and/or a wired or wireless Wide Area Network. In some examples, the healthcare information transport 108 also includes a broker (e.g., a Mitra Imaging's PACS Broker) to allow medical information and medical images to be transmitted together and stored together.

In operation, the healthcare information transport 108 receives images, medical reports, administrative information, and/or other clinical information from the information systems 102, 104, 106 via the interface connections 110, 112 and 114. If necessary (e.g., when different formats of the received information are incompatible), the healthcare information transport 108 translates or reformats (e.g., into Structured Query Language (SQL) or standard text) the medical information, such as medical reports, to be properly stored at the data center 152. Preferably, the reformatted medical information may be transmitted using a transmission protocol to enable different medical information to share common identification elements, such as a patient name or a social security number. Next, the healthcare information transport 108 transmits the medical information to the data center 152 via the data center interface connection 116. Finally, medical information is stored in the data center 152 in, for example, the DICOM format, which enables medical images and corresponding medical information to be transmitted and stored together.

The medical information is later viewable and easily retrievable at one or more of the workstations 154 (e.g., by their common identification element, such as a patient name or a record number). The workstations 154 may be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. The workstations 154 receive commands and/or other inputs from a user via, for example, a microphone, a keyboard, a mouse, a track ball, etc. As shown in FIG. 1B, the workstations 154 are connected to the network 156 and, thus, can communicate with each other, the data center 152, and/or any other device coupled to the network 156. The workstations 154 are capable of implementing a user interface 158 to enable a healthcare practitioner to interact with the medical information system (e.g., the example clinical architecture 100 and the example system architecture 150). For example, in response to a request from a physician, the user interface 158 presents a patient medical history. Additionally, the user interface 158 includes one or more options related to the example methods and apparatus described herein to manage patient information associated with patient encounters.

The example data center 152 of FIG. 1B is an archive to store information such as, for example, images, data, medical reports, and/or, more generally, patient medical records. In addition, the data center 152 may also serve as a central conduit to information located at other sources such as, for example, local archives, hospital information systems (e.g., the hospital information system 102 and/or the clinical system 104), or medical imaging systems (e.g., the RIS/PACS 106). That is, the data center 152 may store links or indicators (e.g., identification numbers, patient names, or record numbers) to information. In the illustrated example, the data center 152 is managed by an application server provider (ASP) and is located in a centralized location that may be accessed by a plurality of systems and facilities (e.g., hospitals, clinics, doctor's offices, other medical offices, and/or terminals). As shown, in some examples, the data center 152 may be spatially distant from the hospital information system 102, the clinical system 104, and/or the RIS/PACS 106 (e.g., at a General Electric® facility). However, in other examples, the data center 152 may be centrally located with the hospital information system 102, the clinical system 104, and/or the RIS/PACS 106 (e.g., at a healthcare facility).

The example data center 152 of FIG. 1B includes a server 160 (e.g., a compute server), a database 162, and a record organizer 164. While the example system architecture 150 of FIG. 1B depicts one server 160 and one data center 162, in other examples, the example system architecture 150 may include any number of data centers (e.g., 1, 2, 3, 4, etc.) and/or any number of servers (e.g., 1, 2, 3, 4, etc.). The server 160 receives, processes, and conveys information to and from the components of the example system architecture 150. The database 162 stores the medical information described herein and provides access thereto. The example record organizer 164 of FIG. 1B manages data associated with medical reports. Specifically, the record organizer 164 identifies and assigns values to encounters associated with the same patient into a medical record or history for the particular patient. Additionally, the record organizer 164 sorts the encounters based on a time at which an encounter occurred. Further, the record organizer 164 changes values assigned to encounters to properly associate them with the same encounter and/or the same patient. Such an approach decreases the likelihood that disjoint information related to encounters is in existence that relate to the same encounter. Thus, a healthcare practitioner (e.g., a physician) is able to review an accurate depiction of a patient's medical record and/or history. Advantageously, the example record organizer 164 enables the healthcare practitioner to more quickly and efficiently review information related to a patient encounter, a patient medical report, record and/or history. Such an approach decreases the likelihood that critical information is missed or mistakenly overlooked. Further, such an approach increases the accuracy and completeness of financial information related to patient encounters (e.g., billing and reimbursement procedures) as well as increasing the accuracy and completeness of medical reports, records and/or histories based on patient encounters. While the examples described herein reference a medical information system, the example methods and systems described herein can be advantageously utilized in any other suitable system such as, for example, financial systems, production control and logistics systems, supply transaction systems, etc., to identify and automatically merge associated encounters.

Figure 2:
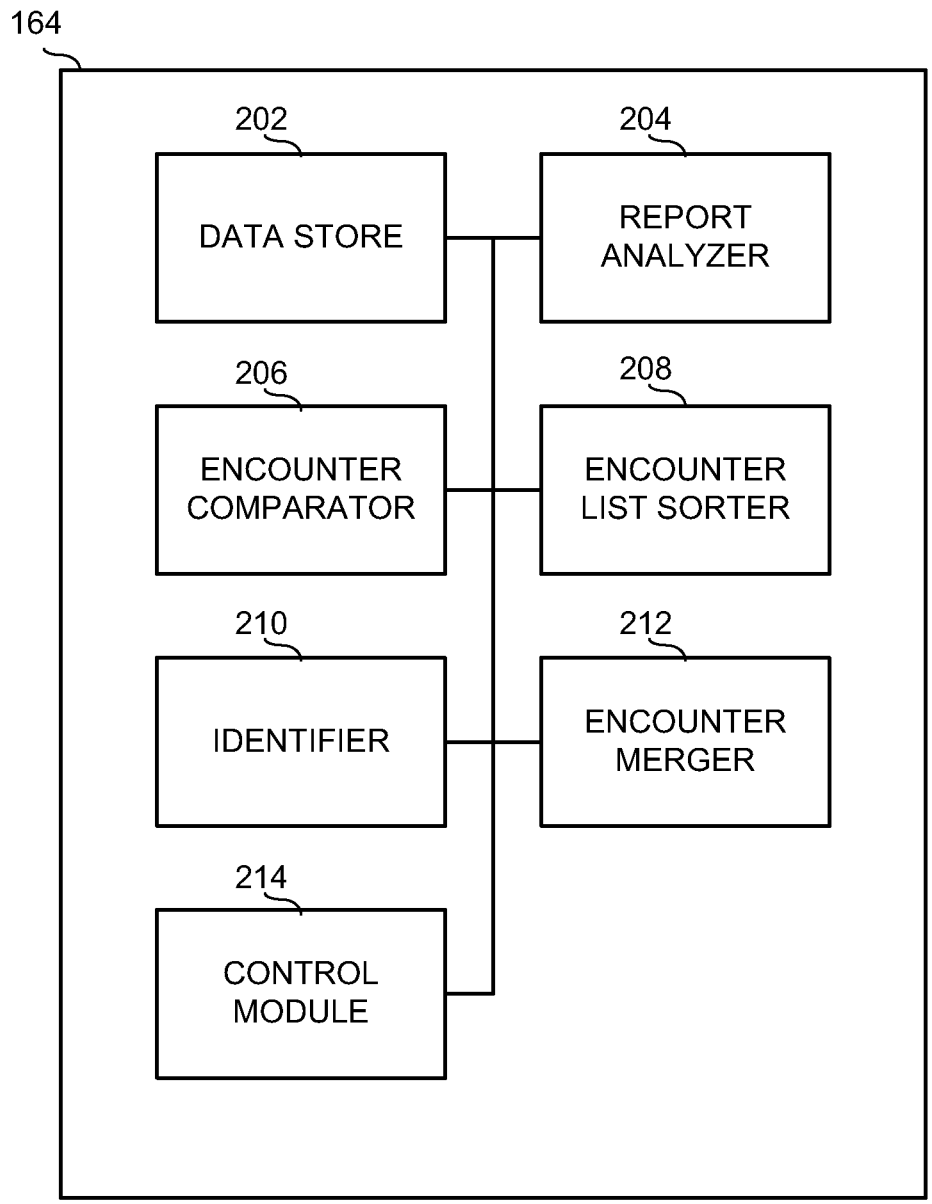
FIG. 2 is a block diagram of an example apparatus that may be used to implement the example record organizer of FIG. 1B.

FIG. 2 is a block diagram of an example apparatus that may be used to implement the record organizer 164 of FIG. 1B. In the illustrated example of FIG. 2, the example record organizer 164 includes a data store 202, a report analyzer 204, an encounter comparator 206, an encounter list sorter 208, an identifier 210, an encounter merger 212 and a control module 214. While an example manner of implementing the record organizer 164 of FIG. 1B has been illustrated in FIG. 2, one or more of the elements, processes and/or devices illustrated in FIG. 2 may be combined, divided, re-arranged, omitted, eliminated and/or implemented in any other way. Specifically, in some examples, the control module 214 may be integrated into each of the data store 202, the report analyzer 204, the encounter comparator 206, the encounter list sorter 208, the identifier 210 and/or the encounter merger 212. Further, the data store 202, the report analyzer 204, the encounter comparator 206, the encounter list sorter 208, the identifier 210, the encounter merger 212, the control module 214 and/or, more generally, the example record organizer 164 of FIG. 2 may be implemented by hardware, software, firmware and/or any combination of hardware, software and/or firmware. Thus, for example, any of the data store 202, the report analyzer 204, the encounter comparator 206, the encounter list sorter 208, the identifier 210, the encounter merger 212, the control module 214 and/or, more generally, the example record organizer 164 of FIG. 2 can be implemented by one or more circuit(s), programmable processor(s), application specific integrated circuit(s) (ASIC(s)), programmable logic device(s) (PLD(s)) and/or field programmable logic device(s) (FPLD(s)), etc. When any of the appended claims are read to cover a purely software and/or firmware implementation, at least one of the data store 202, the report analyzer 204, the encounter comparator 206, the encounter list sorter 208, the identifier 210, the encounter merger 212, the control module 214 and/or, more generally, the example record organizer 164 of FIG. 2 are hereby expressly defined to include a tangible medium such as a memory, DVD, CD, etc., storing the software and/or firmware. Further still, the example record organizer 164 of FIG. 2 may include one or more elements, processes and/or devices in addition to, or instead of, those illustrated in FIG. 2, and/or may include more than one of any or all of the illustrated elements, processes and devices.

To manage patient information associated with patient encounters, the record organizer 164 initially conveys the received patient information to the data store 202. The data store 202 creates a software object to represent the received patient information. The software object includes a plurality of properties that can be altered by, for example, the report analyzer 204, the encounter comparator 206, the encounter list sorter 208, the identifier 210, the encounter merger 212 and/or the control module 214. The data store 202 stores the information associated with a patient encounter(s) and receives and stores the merged and/or identified data as discussed below.

To extract data and/or identifiers from the patient information associated with patient identifications (e.g., a plain text record), the control module 214 retrieves the patient information from the data store 202 and conveys it to the report analyzer 204. In addition, data and/or identifiers may be extracted from electronic medical records (EMRs), optical character recognition (OCR), a medication order system, a database, a computerized physician order entry (CPOE), and/or any other suitable source. The report analyzer 204 may also create a software object to represent the extracted data and/or identifiers from the patient information. The report analyzer 204 implements one or more algorithms capable of scanning the patient information (e.g., information related to different patient identifiers and different encounter identifiers) and identifying one or more keywords, phrases, abbreviations, etc. that are representative of a patient name, a social security number, demographic information, or any other suitable identifying characteristic. If the report analyzer 204 has identified keywords, phrases and/or abbreviations within the patient information, the report analyzer 204 associates the extracted data and/or the patient information with a particular patient, once identified, by assigning a value to the extracted data and/or the patient information that is associated with the particular patient. Once the report analyzer 204 has identified the keywords, phrases and/or abbreviations within the patient information, the extracted data and/or identifiers and the associated values are retrieved by the control module 214 and conveyed to the data store 202 for storage.

To compare the identified keywords, phrases and/or abbreviations associated with a first patient identification (ID) with keywords, phrases and/or abbreviations associated with a second patient identification (ID), the control module 214 retrieves this extracted data from the data store 202 and conveys it to the encounter comparator 206. The encounter comparator 206 compares the extracted data associated with the first patient ID to the extracted data associated with the second patient ID to determine if they are related to the same patient. Specifically, the encounter comparator 206 compares the names, the social security numbers and/or demographic information from the different patient IDs to determine if they are the same or substantially similar. If the encounter comparator 206 has identified that the first patient ID and the second patient ID are associated with the same patient, the encounter comparator 206 associates the first patient ID and the second patient ID by assigning a value to the respective patient ID. Generally, in some instances, some of the keywords, phrases and/or abbreviations are incorrect and, thus, the encounters may be incorrectly associated with numerous patients IDs when in fact they should be associated with the same patient ID.

In practice, due, at least in part, to the atmosphere surrounding some healthcare procedures and/or environments such as, Emergency Rooms, Labor and Delivery or Obstetrics and Gynecology settings, information associated with a particular patient including their name, their social security number and/or their demographic information, (e.g., non-clinical patient information) may be inaccurately and/or incompletely entered into, for example, data fields related to an encounter. To identify these typographical errors, the encounter comparator 206 compares the extracted data and identifies similarities in non-clinical patient information between different patient IDs and, thus, the encounter comparator 206 may be advantageously utilized to identify patient IDs that are incorrectly associated with different patients and/or encounters that are not correctly associated with their corresponding patient medical record and/or history. The encounter comparator 206 may assign a value to the identified discrepancies in the non-clinical patient information to indicate these discrepancies to, for example, a healthcare practitioner. Additionally, the encounter comparator 206 also creates a software object to represent that the particular patient is associated with a patient encounter (e.g., a first encounter, a second encounter, etc.). Once the encounter comparator 206 has compared and identified patient IDs that are associated with the same patient, the patient information along with the associated values are retrieved by the control module 214 and conveyed to the data store 202 for storage.

To sort different encounters associated with the related patient IDs, the control module 214 retrieves the information from the data store 202 and conveys it to the encounter list sorter 208. In practice, in some instances, when information related to an encounter is generated, the encounter is assigned a value to indicate and/or represent the time at which the encounter occurred. The encounter list sorter 208 sorts the encounters associated with the related patient IDs based on the value assigned to the patient information (e.g., the time at which the patient information was recorded). The sorted patient information can be advantageously used in clinical decision support by enabling a healthcare practitioner to receive and/or review chronological accounts (e.g., time oriented episodic views) of the patients' medical treatment(s) and/or ongoing medical procedure(s). Once the encounter list sorter 208 has sorted the patient information, the sorted encounters are retrieved by the control module 214 and conveyed to the data store 202 for storage.

To identify disjoint encounters within the sorted encounters related to a particular patient, the control module 214 retrieves the sorted encounters from the data store 202 and conveys them to the identifier 210. The identifier 210 identifies encounters that are associated with the same encounter. Specifically, the identifier 210 identifies encounters that occurred and/or were generated within approximately the same timeframe. If the identifier 210 has identified that, for example, a first encounter ID and a second encounter ID were assigned on the same day, the identifier 210 may associate the first encounter ID and the second encounter ID by assigning a value to the respective patient ID.

In practice, as discussed in more detail below, due, at least in part, to the atmosphere surrounding some healthcare procedures and/or environments, numerous master records or medical reports, etc. may be generated for a particular patient during a particular encounter (e.g., recording pre-natal fetal waveforms, waveform annotations, and/or patient physiological conditions, etc.). In some examples, a patient may enter a first area of a healthcare facility in need of emergency care. The patient may be assigned a first patient ID and may initially be examined by a first healthcare practitioner who records information that is assigned a first encounter ID (e.g., a first master record). In time, the patient may be transferred to a second area of the hospital and/or assigned a new bed. The patient may then be examined by a second healthcare practitioner that records information that is improperly assigned a second encounter ID (e.g., a second master record). In such instances, the information assigned to the second encounter ID may be disjoint from the information assigned to the first encounter ID even though the information relates to the same encounter.

To magnify the disassociation between the first encounter ID and the second encounter ID, the non-clinical patient information associated with the patient may be inaccurate, incomplete and/or not the same in either report. Specifically, the patient may be assigned a first patient ID by the first healthcare practitioner and a second patient ID by the second healthcare practitioner. Unfortunately, having disjoint information that relates to the same encounter and/or the same patient creates segmented medical reports, records and/or histories, which hinders the fluidity of clinical information and/or exasperates grievances related to financial statements by patients and/or their associated entities. Specifically, these disparities may have adverse effects on the quality of delivered care provided to patients and/or the accuracy of medical bills associated with the encounter(s) because numerous medical bills may be erroneously generated for a procedure, which encompasses many different tasks and/or operations. For instance, in some examples, the bill associated with performing a physical on a patient also includes administering a flu shot to the patient. However, if the doctor performs the physical and records information that is assigned a first encounter ID related to the physical and then the nurse records information that is assigned a second patient ID related to administering the flu shot, a bill for performing the physical will be generated and a bill for administering the flu shot will also be generated. As discussed above, because the bill for performing the physical should have also included administering the flu shot, the additional bill associated with administering the flu shot would be in error. More generally, patients may be repetitiously asked the same questions during an encounter as different healthcare practitioners generate the numerous master records. Once the identifier 210 has identified the disjoint information that is associated with the same encounter within the sorted encounters, the information related to the encounters along with the associated values are retrieved by the control module 214 and conveyed to the data store 202 for storage.

To merge the patient information associated with patient encounters associated with the same patient, the control module 214 retrieves this patient information from the data store 202 and conveys it to the encounter merger 212. Initially, to merge the patient information associated with the same encounter, the encounter merger 212 may merge information assigned to the first encounter ID with the information assigned to the second encounter ID by, for example, changing a value associated with the first encounter ID to be associated with the second encounter ID or by changing a value associated with the second encounter ID to be associated with the first encounter ID to properly associate the encounter ID with a particular encounter. Additionally and/or alternatively, the encounter merger 212 may merge information related to the first patient ID and information related to the second patient ID into a patient medical record and/or history that is associated with the particular patient. Specifically, the identifier 210 identifies the start time and/or the end time of the different encounters and the encounter merger 212 merges the encounters accordingly by changing a value associated with the first patient ID to be associated with the second patient ID or changes a value associated with the second patient ID to be associated with the first patient ID to properly associate the patient ID with a particular patient. Once the encounter merger 212 has merged the patient information associated with patient encounters, the merged encounters and patient information are retrieved by the control module 214 and conveyed to the data store 202 for storage.

The record organizer 164 then conveys the information related to the encounters (e.g., the software object(s) associated with the information related to the encounters), along with the associated values to the database 162 for storage, where they can later be retrieved using one of the workstations 154 (FIG. 1B). Thus, a healthcare practitioner is able to review the information related to the encounters and/or obtain the most relevant information desired by the healthcare practitioner.

The flow diagrams depicted in FIGS. 3, 4, 5, and 6 are representative of machine readable instructions that can be executed to implement the example methods and apparatus described herein. In particular, FIGS. 3, 4, 5, and 6 depict flow diagrams representative of machine readable instructions that may be executed to implement the example record organizer 164 of FIGS. 1B and/or 2 to manage patient information associated with patient encounters. The example processes of FIGS. 3, 4, 5, and 6 may be performed using a processor, a controller and/or any other suitable processing device. For example, the example processes of FIGS. 3, 4, 5, and 6 may be implemented in coded instructions stored on a tangible medium such as a flash memory, a read-only memory (ROM) and/or random-access memory (RAM) associated with a processor (e.g., an example processor system 1500 discussed below in connection with FIG. 15). Alternatively, some or all of the example processes of FIGS. 3, 4, 5, and 6 may be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIGS. 3, 4, 5, and 6 may be implemented manually or as any combination(s) of any of the foregoing techniques, for example, any combination of firmware, software, discrete logic and/or hardware. Further, although the example processes of FIGS. 3, 4, 5, and 6 are described with reference to the flow diagrams of FIGS. 3, 4, 5, and 6 other methods of implementing the processes of FIGS. 3, 4, 5, and 6 may be employed. For example, the order of execution of the blocks may be changed, and/or some of the blocks described may be changed, eliminated, sub-divided, or combined. Additionally, any or all of the example processes of FIGS. 3, 4, 5, and 6 may be performed sequentially and/or in parallel by, for example, separate processing threads, processors, devices, discrete logic, circuits, etc.

Figure 3:
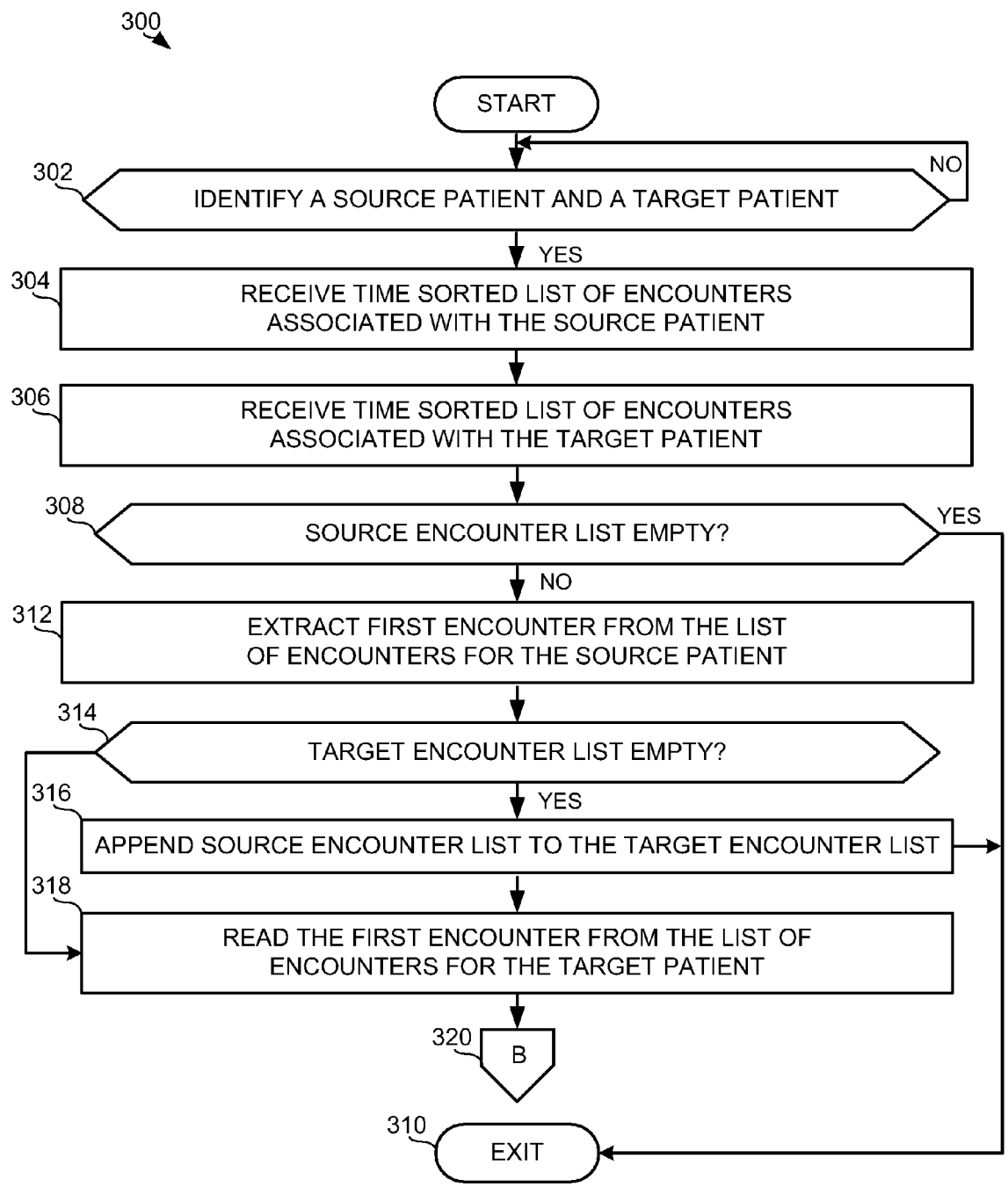
FIG. 3 is a flow diagram representative of example machine readable instructions that may be executed to implement an initialization process of the example record organizer of FIGS. 1 and/or 2.

FIG. 3 depicts an example initialization process 300 that may be used to implement the examples described herein. Initially the record organizer 164 (FIGS. 1B and 2) identifies a source patient (e.g., a patient ID 1) and a target patient (e.g., patient ID 2) (block 302). Specifically, the record organizer 164 (FIGS. 1B and 2) receives information and the report analyzer 204 (FIG. 2) identifies and extracts information representative of keywords, phrases and/or abbreviations, etc. that are associated with at least one of a name, a social security number and/or demographic information. Additionally, the report analyzer 204 (FIG. 2) may assign a value to the source patient and/or the target patient, once identified.

If the source patient and the target patient are identified by the comparator 206 (FIG. 2) as being associated with the same patient, the record organizer 164 (FIGS. 1B and 2)

receives a time sorted list of encounters associated with the source patient (block 304) and a time sorted list of encounters associated with the target patient (block 306) from, for example, the encounter list sorter 208 (FIG. 2). As discussed above, each of the encounters within the list is assigned an encounter ID and a patient ID. Next the identifier 210 (FIG. 2) identifies if the source encounter list is empty (block 308).

If the identifier 210 (FIG. 2) identifies that the source encounter list is empty, the example process is exited (block 310). However, if the identifier 210 (FIG. 2) identifies that the source encounter list is not empty, the control module 214 (FIG. 2) extracts the first encounter, having an encounter ID, from the source encounter list (block 312). Specifically, extracting the first encounter from the source encounter list will remove the first encounter from the head of the list and return it and, thus, the reading position is advanced to the next encounter in the source encounter list, which is the now the head of the list.

The identifier 210 (FIG. 2) then identifies if the target list is empty (block 314). If the identifier 210 (FIG. 2) identifies that the target encounter list is empty, the encounter merger 212 appends the source encounter list to the target encounter list (block 316) and then the example process is exited (block 310). Specifically, the encounter merger 212 may change the patient ID of the encounters associated with the source patient to the patient ID associated with the target patient. However, if the identifier 210 (FIG. 2) identifies that the target encounter list is not empty, the report analyzer 204 (FIG. 2) reads the first encounter, having an encounter ID, from the target encounter list (block 318) and then control moves to B (block 320), a process that is discussed below in connection with FIG. 4.

Figure 4:
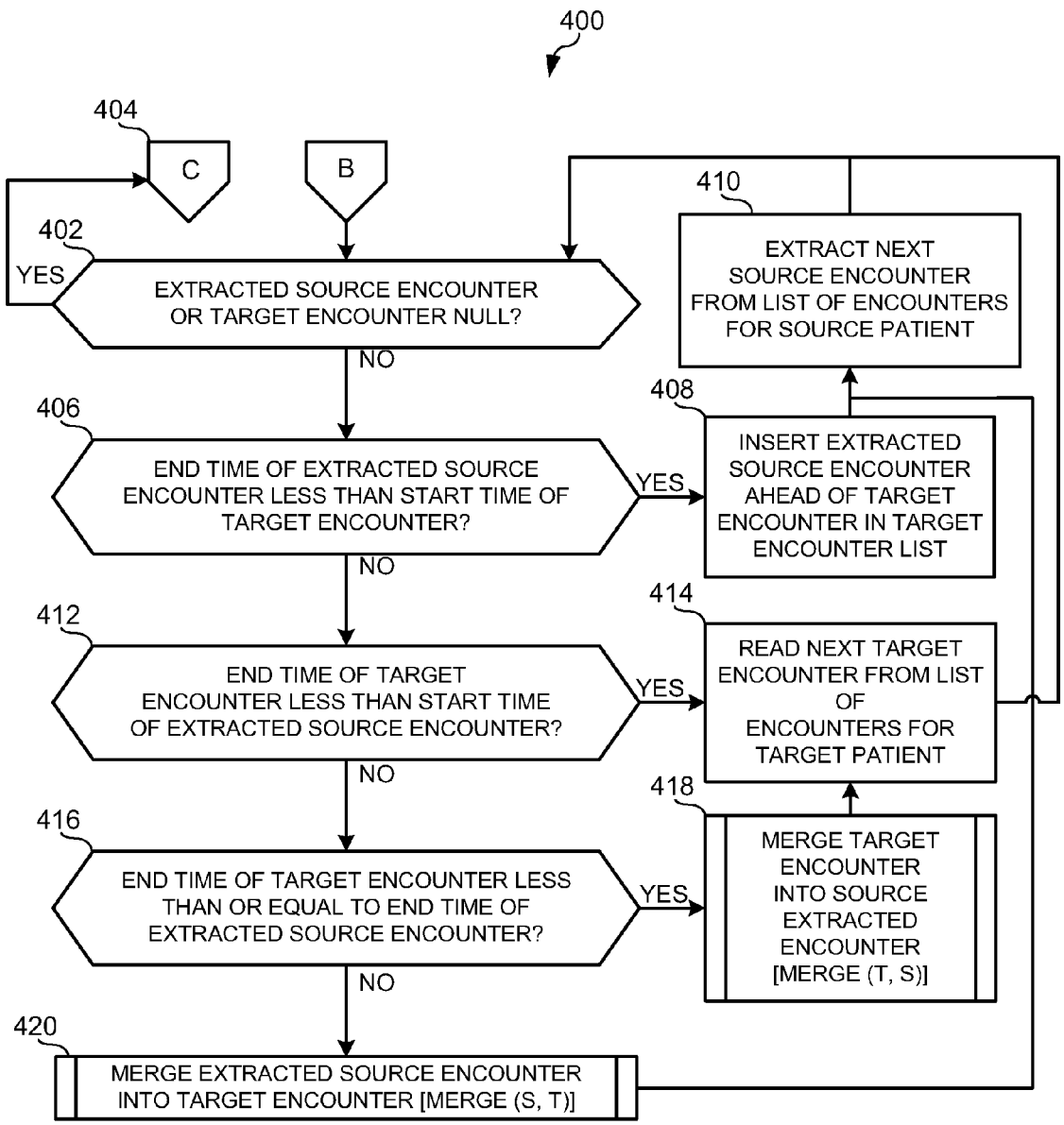
FIG. 4 is a flow diagram representative of example machine readable instructions that may be executed to implement a post initialization process of the example record organizer of FIGS. 1 and/or 2.

FIG. 4 depicts an example main process and/or post initialization process 400 that may be used to implement the examples described herein. Initially, the identifier 210 (FIG. 2) identifies if the extracted source encounter from the source encounter list is null or if the read encounter from the list of encounters for the target patient is null (block 402). If either of the extracted source encounter or the read encounter from the list of encounters for the target patient are null, control moves to C (block 404), a process that is discussed below in connection with FIG. 6.

However, if the extracted source encounter from the source encounter list and the read encounter from the list of encounters for the target patient are not null, the identifier 210 (FIG. 2) identifies if the end time of the extracted source encounter is less than the start time of the read target encounter (block 406). If the end time of the extracted source encounter is less than the start time of the read target encounter, the encounter merger 212 (FIG. 2) inserts the extracted source encounter ahead of the read target encounter in the target encounter list (block 408). Specifically, the encounter merger 212 (FIG. 2) changes the patient ID associated with the extracted source encounter to be associated with the patient ID associated with the target patient. Next, the control module 214 (FIG. 2) extracts the next source encounter from the list of encounters for the source patient (block 410) and control moves back to block 402.

However, if the end time of the extracted source encounter is not less than the start time of the read target encounter, control moves to block 412. Specifically, the identifier 210 (FIG. 2) identifies if the end time of the read target encounter is less than the start time of the extracted source encounter (block 412). If the end time of the read target encounter is less than the start time of the extracted source encounter, the report analyzer 204 (FIG. 2) reads the next target encounter from the list of encounters for the target patient (block 414) and control then moves back to block 402.

However, if the end time of the read target encounter is not less than the start time of the extracted source encounter, control moves to block 416. Specifically, the identifier 210 (FIG. 2) identifies if the end time of the read target encounter is less than or equal to the end time of the extracted source encounter (block 416). If the end time of the read target encounter is less than or equal to the end time of the extracted source encounter, the encounter merger 212 (FIG. 2) merges the read target encounter into the extracted source encounter (block 418) as discussed in more detail below in connection with FIG. 5 and control then moves to block 414. However, if the end time of the read target encounter is not less than or equal to the end time of the extracted source encounter, the encounter merger 212 (FIG. 2) merges the extracted source encounter into the read target encounter (block 420) as discussed in more detail below in connection with FIG. 5 and control then moves to block 410.

Figure 5:
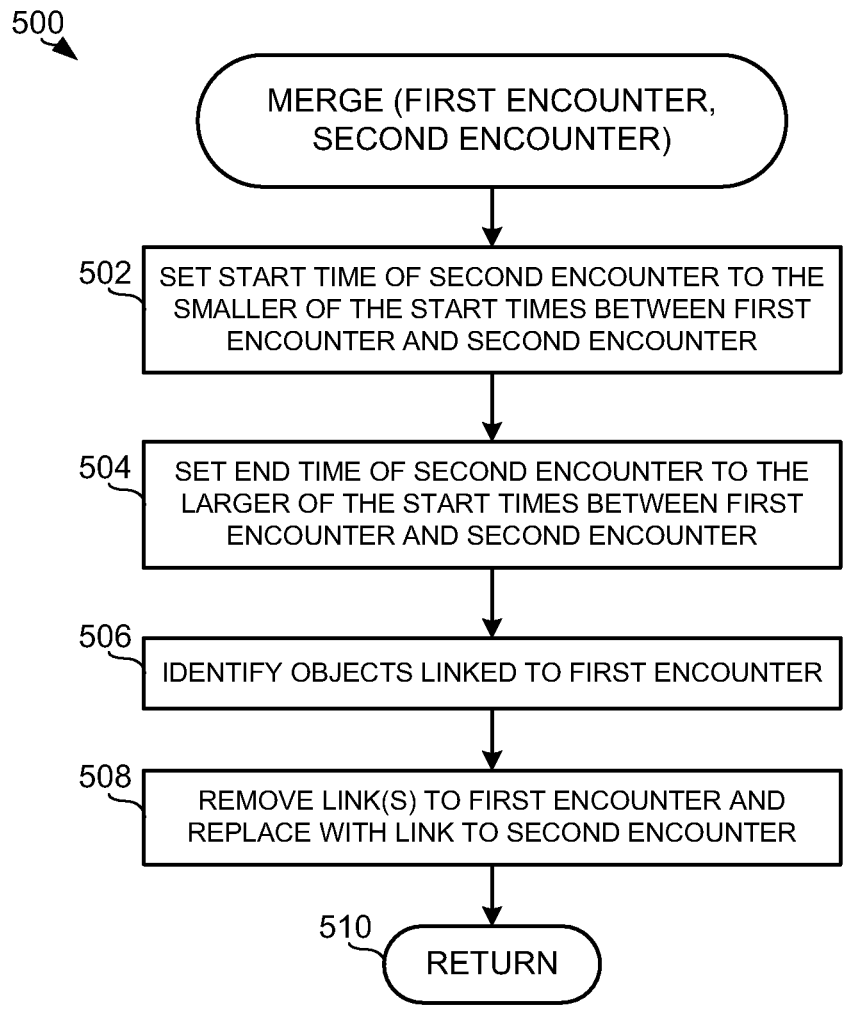
FIG. 5 is a flow diagram representative of example machine readable instructions that may be executed to implement a merge process of the example record organizer of FIGS. 1 and/or 2.

FIG. 5 depicts an example merge process 500 that may be used to implement the examples described herein. Specifically, the example merge process 500 may be used to merge the encounters as discussed above in connection with blocks 418 and 420. Initially, the encounter merger 212 (FIG. 2) sets the start time of the second encounter, which is the extracted source encounter for block 418 and the read target encounter for block 420, to the smaller of the start times between the first encounter and the second encounter (block 502). Next, the encounter merger 212 (FIG. 2) sets the end time of the second encounter to the larger of the start times between the first encounter and the second encounter (block 504).

The identifier 210 (FIG. 2) then identifies objects such as, for example, fetal strips, annotations, observations, medications, allergies, problems, orders, procedures, etc., that are linked to the first encounter (block 506). Specifically, the identifier 210 (FIG. 2) identifies objects that have an encounter ID associated with the first encounter. The encounter merger 212 (FIG. 2) then removes the link(s) to the first encounter and replaces the removed link with a link to the second encounter (block 508). Specifically, the encounter merger 212 (FIG. 2) replaces the encounter ID that is associated with the first encounter with an encounter ID that is associated with the second encounter. Control then moves to either block 414 (FIG. 4) if the merge process 500 merged the target encounter into the extracted source encounter or to block 410 (FIG. 4) if the merge process 500 merged the extracted source encounter into the read target encounter (block 510).

Figure 6:
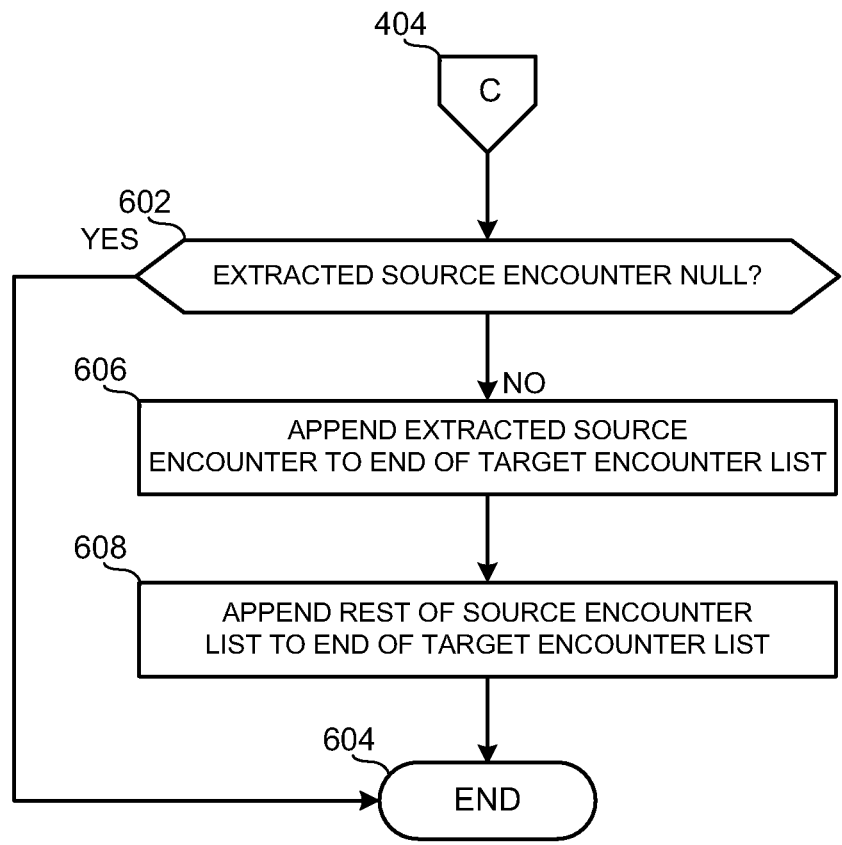
FIG. 6 is a flow diagram representative of example machine readable instructions that may be executed to implement a finalization process of the example record organizer of FIGS. 1 and/or 2.

FIG. 6 depicts an example finalization process 600 that may be used to implement the examples described herein. Initially, the identifier 210 (FIG. 2) identifies if the extracted source encounter is null (block 602). If the identifier 210 (FIG. 2) identifies that the extracted source encounter is null, the example finalization process 600 is ended (block 602). However, if the identifier 210 (FIG. 2) identifies that the extracted source encounter is not null, the encounter merger 212 (FIG. 2) appends the extracted source encounter to the end of the target list encounter (block 606). Next the encounter merger 212 (FIG. 2) appends the remainder of the source encounter list to the end of the target encounter list (block 608). Specifically, for blocks 606 and 608, the encounter merger 212, may change the patient ID of the encounters associated with the source patient to the patient ID associated with the target patient.

FIGS. 7 through 14 are representative of various example scenarios in which two encounter IDs are associated with a first patient identifier (ID) and a second patient identifier (ID)

that are actually associated with the same patient. Specifically, as discussed above, in some instances, non-clinical patient information is inaccurately recorded and, thus, two patient IDs may exist for a particular patient and/or two encounter IDs may exist for a particular encounter. In practice, having disjoint encounters and/or numerous patient IDs for a particular patient may prevent healthcare practitioners from accurately monitoring the quality of delivered care, result in unnecessary duplicative patient testing and/or create multiple bills associated with the same encounter. Additionally, if numerous encounter IDs exist for an encounter, an auditor may not be able to readily identify that a healthcare practitioner performed all of the proper procedures during an examination such as, for example, the auditor may not be able to verify that a physician checked the feet of a patient having diabetes to verify the absence of complications related to the diabetes.

As discussed above, initially, the report analyzer 204 (FIG. 2) analyzes patient information related to different patient IDs to identify and extract information (e.g., via an OCR process) related to a name, a social security number and/or demographic information. Additionally, the report analyzer 204 (FIG. 2) may assign a value to each patient ID that is associated with a particular patient, once identified. The encounter comparator 206 (FIG. 2) then compares the extracted information from various patient IDs to identify if they are associated with the same patient. If the medical reports are associated with the same patient, the encounter list sorter 208 then sorts the encounters associated with patient ID 1 and patient ID 2 in chronological order based on the time at which the encounter occurred and/or the related information was recorded.

Figure 7:
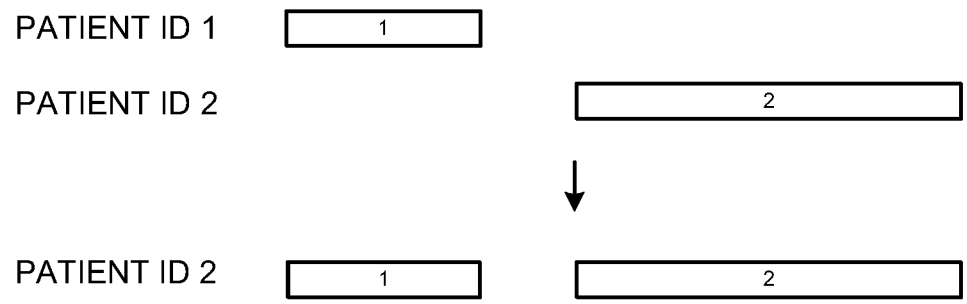
FIGS. 7-14 depict examples of various scenarios in which two sets of medical records exist that are associated with a first patient identifier and a second patient identifier.

FIG. 7 depicts an example in which patient ID 1 and patient ID 2 were identified by the encounter comparator 206 (FIG. 2) as being associated with the same patient. Patient information associated with patient ID 1 is related to encounter ID 1 and patient information associated with patient ID 2 is related to encounter ID 2. In this example, since the identifier 210 (FIG. 2) has not identified that encounter ID 1 and encounter ID 2 are associated with the same encounter, initially, the identifier 210 identifies if the end of encounter ID 1 that is related to patient ID 1 occurred at a time before (e.g., is less than) the start encounter ID 2 that is related to patient ID 2. In this example, the end of encounter ID 1 occurred at a time before the start of encounter ID 2 and, thus, the encounter merger 212 merges patient ID 1 and patient ID 2 by changing a corresponding value associated with patient ID 1 to be associated with patient ID 2, such that, encounter ID 1 and encounter ID 2 are now associated with patient ID 2.

Figure 8:
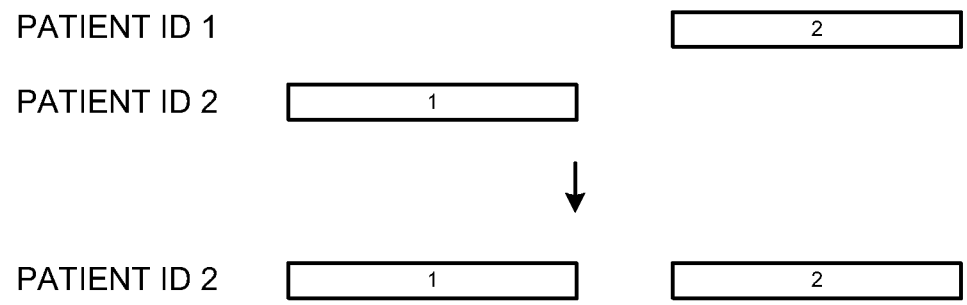

FIG. 8 depicts another example in which patient ID 1 and patient ID 2 were identified by the encounter comparator 206 (FIG. 2) as being associated with the same patient. Patient information associated with patient ID 1 is related to encounter ID 2 and patient information associated with patient ID 2 is related to encounter ID 1. In this example, since the identifier 210 (FIG. 2) has not identified that encounter ID 1 and encounter ID 2 are associated with the same encounter, initially, the identifier 210 (FIG. 2) identifies if the end of encounter ID 2 related to patient ID 1 occurred at a time before the start of encounter ID 1 related to patient ID 2. In this example, the end of encounter ID 2 occurred at a time after the start of encounter ID 1 and, thus, the identifier 210 then identifies if the end of encounter ID 1 related to patient ID 2 occurred at a time before the start of encounter ID 2 related to patient ID 1. In this example, the end of encounter ID 1 occurred at a time before the start of encounter ID 2 and, thus, the encounter merger 212 merges patient ID 1 and patient ID 2 by changing a corresponding value associated with patient ID 2 to be associated with patient ID 2, such that, encounter ID 1 and encounter ID 2 are now associated with patient ID 2.

Figure 9:
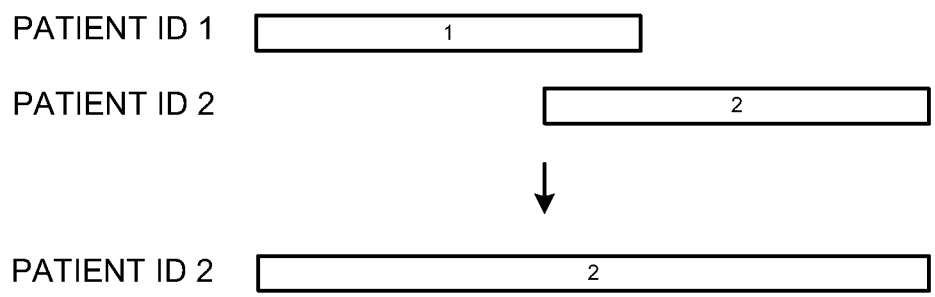

FIG. 9 depicts another example in which patient ID 1 and patient ID 2 were identified by the encounter comparator 206 (FIG. 2) as being associated with the same patient. Patient information associated with patient ID 1 is related to encounter ID 1 and patient information associated with patient ID 2 is related to encounter ID 2. In this example, the identifier 210 (FIG. 2) has identified that encounter ID 1 and encounter ID 2 are associated with the same encounter. Depending on whether the end of the encounter ID associated with patient ID 1 occurred at a time before or after the end of the encounter ID associated with patient ID 2, the encounter merger 212 will merge the encounter IDs associated with the same encounter into a merged encounter ID and associate the merged encounter ID with either patient ID 1 or patient ID 2. Specifically, if the end of the encounter ID that is related to patient ID 1 occurred at a time before the end of the encounter ID that is related to patient ID 2, the encounter merger 212 merges the encounter IDs associated with the same encounter into a merged encounter ID and associates the merged encounter ID with patient ID 2. Alternatively, if the end of the encounter ID that is related to patient ID 2 occurred at a time before the end of the encounter ID related to patient ID 1, the encounter merger 212 merges the encounters IDs associated with the same encounter into a merged encounter ID and associates the merged encounter ID with patient ID 1. In this example, the end of the encounter ID 1 that is related to patient ID 1 occurred at a time before the end of the encounter ID 2 that is related to patient ID 2 and, therefore, the encounter merger 212 merges encounter ID 1 and encounter ID 2 by changing a value associated with encounter ID 1 to be associated with encounter ID 2 and by changing a corresponding value associated with patient ID 1 to be associated with patient ID 2, such that, encounter ID 1 and encounter ID 2 are now both associated with encounter ID 2 and patient ID 2.

Figure 10:
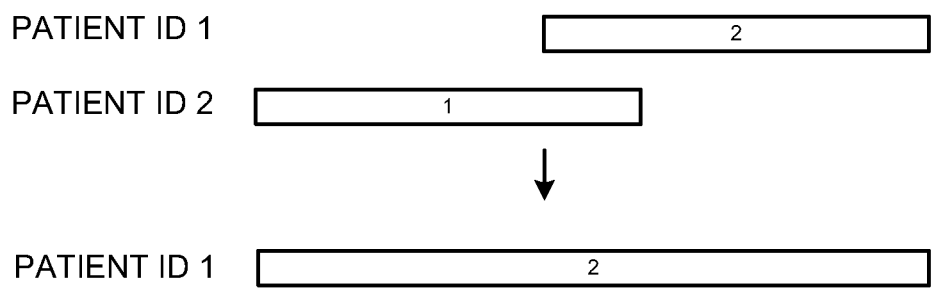

FIG. 10 depicts another example in which patient ID 1 and patient ID 2 were identified by the encounter comparator 206 (FIG. 2) as being associated with the same patient. Patient information associated with patient ID 1 is related to encounter ID 2 and patient information associated with patient ID 2 is related to encounter ID 1. In this example, the identifier 210 (FIG. 2) has identified that encounter ID 1 and encounter ID 2 are associated with the same encounter. In this example, the end of encounter ID 2 that is related to patient ID 1 occurred at a time after the end of the encounter ID 1 that is related to patient ID 2 and, therefore, the encounter merger 212 merges encounter ID 1 and encounter ID 2 by changing a corresponding value associated with encounter ID 1 to be associated with encounter ID 2 and by changing a corresponding value associated with patient ID 2 to be associated with patient ID 1, such that, encounter ID 1 and encounter ID 2 are now both associated with encounter ID 2 and patient ID 1.

Figure 11:
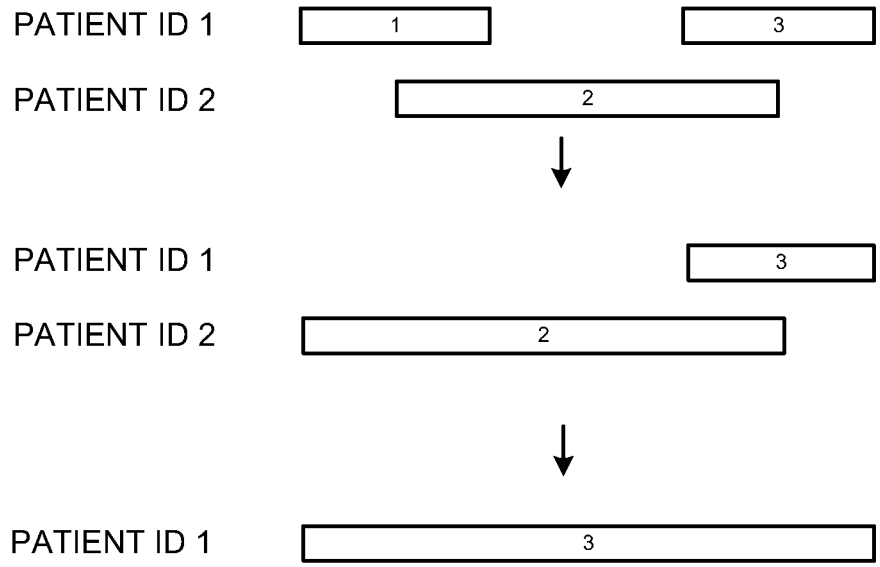

FIG. 11 depicts another example in which patient ID 1 and patient ID 2 were identified by the encounter comparator 206 (FIG. 2) as being associated with the same patient. Patient information associated with patient ID 1 is related to encounter ID 1 and encounter ID 3 and patient information associated with patient ID 2 is related to encounter ID 2. In this example, the identifier 210 (FIG. 2) has identified that encounter ID 1, encounter ID 2 and encounter ID 3 are associated with the same encounter. In this example, initially, the identifier 210 identifies if the end of encounter ID 1 that is related to patient ID 1 occurred at a time before the end of encounter ID 2 that is related to patient ID 2. Because the end of encounter ID 1 occurred at a time before the end of encounter ID 2, the encounter merger 212 merges encounter ID 1 and encounter ID 2 by changing a value associated with encounter ID 1 to be associated with encounter ID 2 and by changing a corresponding value associated with patient ID 1 to be associated with patient ID 2, such that, encounter ID 1 and encounter ID 2 are now both associated with encounter ID 2 and patient ID 2. Next, the identifier 210 (FIG. 2) identifies if the end of encounter ID 3 related to patient ID 1 occurred at a time before the end of encounter ID 2 related to patient ID 2. In this example, encounter ID 3 occurred at a time after encounter ID 2 and, thus, the encounter merger 212 then identifies if the end of encounter ID 2 related to patient ID 2 occurred at a time before the end of encounter ID 3 related to patient ID 1. Because the end of encounter ID 2 occurred at a time before the end of encounter ID 3, the encounter merger 212 merges encounter ID 2 and encounter ID 3 by changing a value associated with encounter ID 2 to be associated with encounter ID 3 and by changing a corresponding value associated with patient ID 2 to be associated with patient ID 1, such that, encounter ID 2 and encounter ID 3 are now both associated with encounter ID 3 and patient ID 1.

Figure 12:
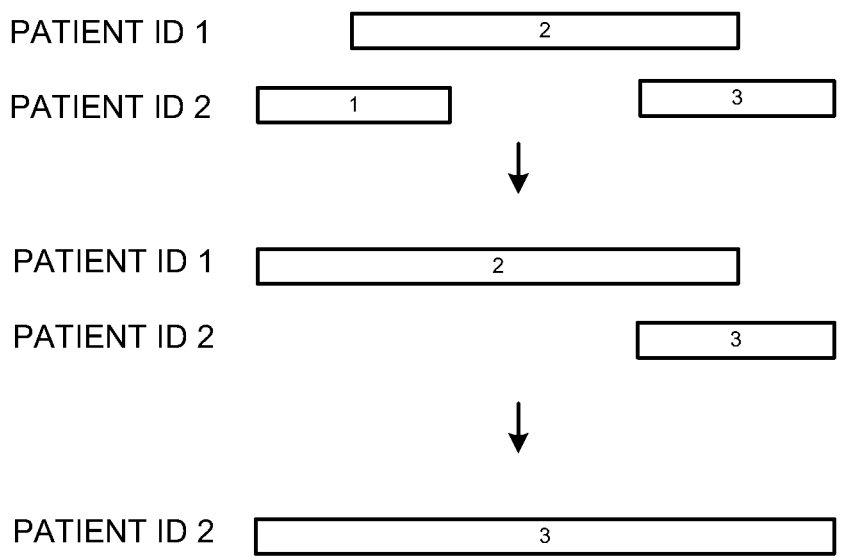

FIG. 12 depicts another example in which patient ID 1 and patient ID 2 were identified by the encounter comparator 206 (FIG. 2) as being associated with the same patient. Patient information associated with patient ID 1 is related to encounter ID 2 and patient information associated with patient ID 2 is related to encounter ID 1 and encounter ID 3. In this example, the identifier 210 (FIG. 2) has identified that encounter ID 1, encounter ID 2 and encounter ID 3 are associated with the same encounter. In this example, initially, the identifier 210 identifies if end of encounter ID 2 that is related to patient ID 1 occurred at a time before the end of encounter ID 1 that is related to patient ID 2. Because the end of encounter ID 2 occurred at a time after the end of encounter ID 1, the encounter merger 212 merges encounter ID 1 and encounter ID 2 by changing a value associated with encounter ID 1 to be associated with encounter ID 2 and by changing a corresponding value associated with patient ID 2 to be associated with patient ID 1, such that, encounter ID 1 and encounter ID 2 are now both associated with encounter ID 2 and patient ID 1. Next, the identifier 210 (FIG. 2) identifies if the end of encounter ID 2 related to patient ID 1 occurred at a time before the end of encounter ID 3 related to patient ID 2. In this example, the end of encounter ID 2 occurred at a time before the end of encounter ID 3 and, thus, the encounter merger 212 merges encounter ID 2 and encounter ID 3 by changing a value associated with encounter ID 2 to be associated with encounter ID 3 and by changing a corresponding value associated with patient ID 1 to be associated with patient ID 2, such that, encounter ID 2 and encounter ID 3 are now both associated with encounter ID 3 and patient ID 2.

Figure 13:
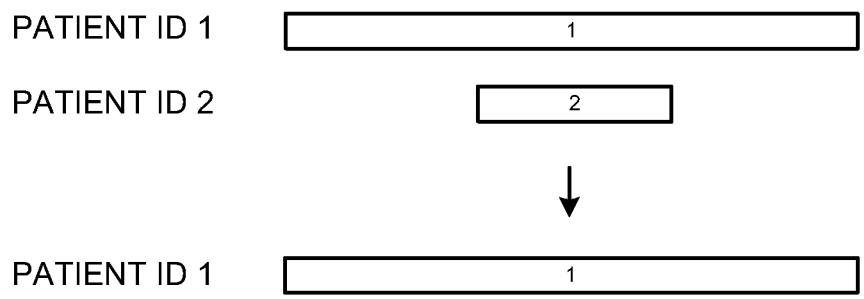

FIG. 13 depicts another example in which patient ID 1 and patient ID 2 were identified by the encounter comparator 206 (FIG. 2) as being associated with the same patient. Patient information associated with patient ID 1 is related to encounter ID 1 and patient information associated with patient ID 2 is related to encounter ID 2. In this example, the identifier 210 (FIG. 2) has identified that encounter ID 1 and encounter ID 2 are associated with the same encounter. In this example, the end of encounter ID 1 that is related to patient ID 1 occurred at a time after the end of encounter ID 2 that is related to patient ID 2 and, thus, the encounter merger 212 merges encounter ID 1 and encounter ID 2 by changing a value associated with encounter ID 2 to be associated with encounter ID 1 and by changing a corresponding value associated with patient ID 2 to be associated with patient ID 1, such that, encounter ID 1 and encounter ID 2 are now both associated with encounter ID 1 and patient ID 1.

Figure 14:
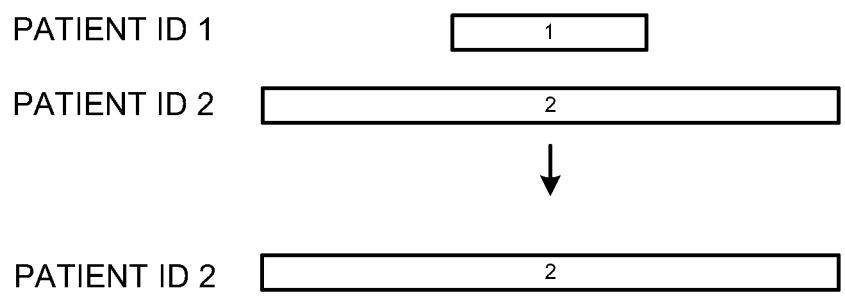

FIG. 14 depicts another example in which patient ID 1 and patient ID 2 were identified by the encounter comparator 206 (FIG. 2) as being associated with the same patient. Patient information associated with patient ID 1 is related to encounter ID 1 and patient information associated with patient ID 2 is related to encounter ID 2. In this example, the identifier 210 (FIG. 2) has identified that encounter ID 1 and encounter ID 2 are associated with the same encounter. In this example, the end of encounter ID 2 that is related to patient ID 2 occurred at a time after the end of encounter ID 1 that is related to patient ID 1 and, thus, the encounter merger 212 merges encounter ID 1 and encounter ID 2 by changing a value associated with encounter ID 1 to be associated with encounter ID 2 and by changing a corresponding value associated with patient ID 1 to be associated with patient ID 2, such that, encounter ID 1 and encounter ID 2 are now both associated with encounter ID 2 and patient ID 2.

Figure 15:
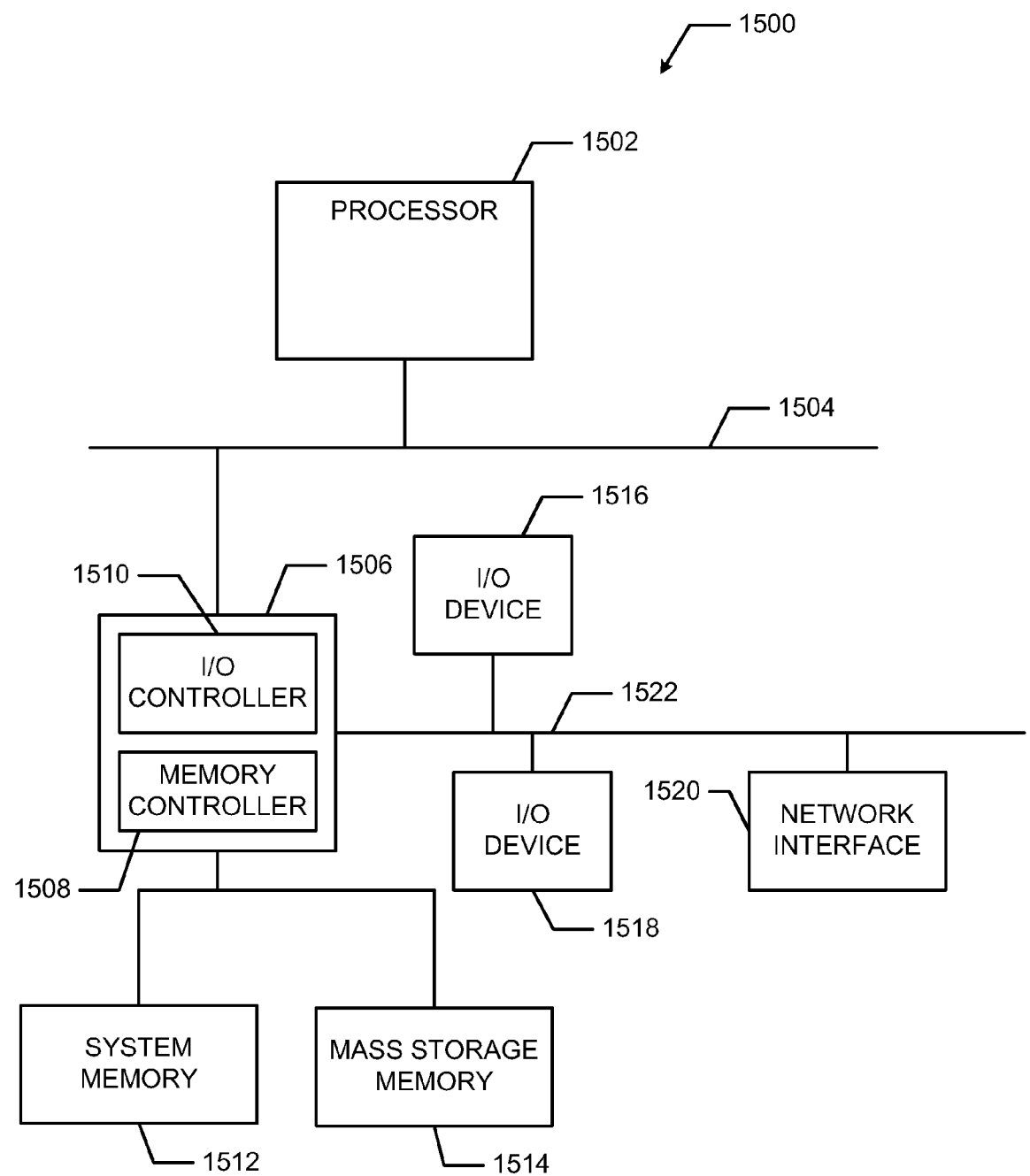
FIG. 15 is a block diagram of an example processor system that may be used to execute the machine readable instructions of FIG. 3-6 to implement the example record organizer of FIG. 2.

FIG. 15 is a block diagram of the example processor system 1500 that may be used to implement the apparatus and methods described herein. As shown in FIG. 15, the processor system 1500 includes a processor 1502 that is coupled to an interconnection bus 1504. The processor 1502 may be any suitable processor, processing unit or microprocessor. Although not shown in FIG. 6, the processor system 1500 may be a multi-processor system and, thus, may include one or more additional processors that are identical or similar to the processor 1502 and that are communicatively coupled to the interconnection bus 1504.

The processor 1502 of FIG. 15 is coupled to a chipset 1506, which includes a memory controller 1508 and an input/output (I/O) controller 1510. As is well known, a chipset typically provides I/O and memory management functions as well as a plurality of general purpose and/or special purpose registers, timers, etc. that are accessible or used by one or more processors coupled to the chipset 1506. The memory controller 1508 performs functions that enable the processor 1502 (or processors if there are multiple processors) to access a system memory 1512 and a mass storage memory 1514.

The system memory 1512 may include any desired type of volatile and/or non-volatile memory such as, for example, static random access memory (SRAM), dynamic random access memory (DRAM), flash memory, read-only memory (ROM), etc. The mass storage memory 1514 may include any desired type of mass storage device including hard disk drives, optical drives, tape storage devices, etc.

The I/O controller 1510 performs functions that enable the processor 1502 to communicate with peripheral input/output (I/O) devices 1516 and 1518 and a network interface 1520 via an I/O bus 1522. The I/O devices 1516 and 1518 may be any desired type of I/O device such as, for example, a keyboard, a video display or monitor, a mouse, etc. The network interface 1520 may be, for example, an Ethernet device, an asynchronous transfer mode (ATM) device, an 802.11 device, a DSL modem, a cable modem, a cellular modem, etc. that enables the processor system 1500 to communicate with another processor system.

While the memory controller 1508 and the I/O controller 1510 are depicted in FIG. 6 as separate blocks within the chipset 1506, the functions performed by these blocks may be integrated within a single semiconductor circuit or may be implemented using two or more separate integrated circuits.

Certain example implementations contemplate methods, systems and computer program products on any machine-readable media to implement functionality described above. Certain example implementations may be implemented using an existing computer processor, or by a special purpose computer processor incorporated for this or another purpose or by a hardwired and/or firmware system, for example.

Certain example implementations include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

The example methods and apparatus described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. The example methods and apparatus described herein may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

What is claimed is:

1. A computer-implemented method to manage patient information in a medical information system, comprising:
   scanning, using a computer, first information comprising a first patient identification associated with a first value and a first encounter identification to extract first non-clinical information, using a computer, the first information comprising first clinical information and the first non-clinical information;
   scanning, using a computer, second information comprising a second patient identification associated with a second value and a second encounter identification to extract second non-clinical information, using a computer, the second information comprising second clinical information and the second non-clinical information;
   comparing at least the extracted first non-clinical information to the extracted second non-clinical information, using a computer, to detect that at least a portion of the first non-clinical information is the same or similar to the second non-clinical information to detect that the first patient identification and the second patient identification are associated with the same patient;
   in response to detecting that the first patient identification and the second patient identification are associated with the same patient, detecting that the first information and the second information are associated with the same encounter based at least in part on a comparison of a first time period associated with the first information and a second time period associated with the second information, the first clinical information is at least partially different from the second clinical information, the first time period at least partially overlapping the second time period; and
   in response to detecting that the first encounter identification and the second encounter identification are associated with the same encounter, merging the first non-clinical information and the second non-clinical information and merging the at least partially different first and second clinical information, using a computer.

2. The method as defined in claim 1, wherein the first patient identification is associated with a source patient and the second patient identification is associated with a target patient and wherein the first encounter identification is an encounter within a source encounter list and the second encounter identification is an encounter within a target encounter list.

3. The method as defined in claim 1, further comprising adjusting a patient billing based on detecting that the first encounter identification and the second encounter identification are associated with the same encounter.

4. The method as defined in claim 1, further comprising monitoring a quality of delivered care to a patient based on detecting that the first information and the second information are associated with at least one of the same patient or the same encounter.

5. The method as defined in claim 1, further comprising implementing a user interface capable of conveying information that is associated with a patient.

6. The method as defined in claim 1, further comprising enabling a healthcare practitioner to query a data store using the extracted information comprising providing a search function capable of using one or more values associated with the extracted information as search criteria.

7. The method as defined in claim 1, wherein merging the first clinical information and the second clinical information comprises changing a third value associated with the first encounter identification to be a fourth value associated with the second encounter identification or by changing the fourth value associated with the second encounter identification to be the third value associated with the first encounter identification.

8. The method of claim 1, further comprising, based on detecting that the first patient identification and the second patient identification are associated with the same patient, associating the first information and the second information with the same patient identification, using a computer, by changing the first value associated with the first patient identification to be the second value associated with the second patient identification or by changing the second value associated with the second patient identification to be the first value associated with the first patient identification.

9. The method as defined in claim 1, wherein merging the first clinical information and the second clinical information comprises detecting a first end time of the first time period being after a second end time of the second time period and, in response to detecting the first end time being after the second end time, changing a third value associated with the second encounter identification to be a fourth value associated with the first encounter identification.

10. A medical information system, comprising:
a computer, comprising:
a data store, implemented using a tangible computer readable storage medium, in communication with one or more data entry systems to receive and store healthcare data transmitted from the one or more data entry systems;
a report analyzer to extract data associated with at least one of patient identifications or patient encounter identifications, different patient identifications associated with different values, wherein the data comprises non-clinical information and clinical information, the non-clinical information comprises at least one of non-clinical patient information, a name, a social security number, demographic information, or a time related to the patient encounter identification;
a comparator to compare at least the extracted non-clinical information associated with the different patient identifications and time periods associated with the patient encounter identifications to determine if the different patient identifications are associated with the same patient and to determine if the patient encounter identifications are associated with the same encounter based at least in part on the time periods associated with the respective encounter identifications being within a predetermined threshold, the clinical information associated with the different patient identifications comprising at least partially different clinical information, the time periods at least partially overlapping;
a record merger to at least associate different patient identifications with the same patient identification when the respective patient identifications are associated with the same patient by changing the value associated with the different patient identifications to be the same value and to associate different patient encounter identifications associated with at least partially different clinical information with the same patient encounter identification when the respective patient encounter identifications are associated with the same encounter.

11. The medical information system as defined in claim 10, further comprising an identifier to identify patient encounter identifications that are associated with the same encounter.

12. The medical information system as defined in claim 10, further comprising one or more workstations in communication with the data store, wherein the workstations implement a user interface to enable a healthcare practitioner to query the data store using one or more values associated with the extracted data.

13. The medical information system as defined in claim 10, further comprising one or more workstations in communication with the data store, wherein the workstations implement a user interface to enable a healthcare practitioner to generate a medical report associated with healthcare data based on another encounter with a patient.

14. The medical information system as defined in claim 10, further comprising software objects stored in the data store to represent the healthcare data.

15. The medical information system as defined in claim 10, further comprising storage properties stored in association with the healthcare data, wherein the storage properties are based on at least some of the extracted data.

16. A tangible machine accessible storage device having instructions stored thereon that, when executed, cause a machine to:
analyze first information stored in a medical information system to extract first non-clinical information, the first information comprising the first non-clinical information, first clinical information, and a first patient identification associated with a first value;
analyze second information stored in a medical information system to extract second non-clinical information, the second information comprising the second non-clinical information, second clinical information, and a second patient identification associated with a second value;
compare at least the extracted first non-clinical information and the extracted second non-clinical information;
based on the comparison, detect that the first patient identification and the second patient identification are associated with the same patient based on at least a portion of the first non-clinical information being the same or similar to the second non-clinical information;
based on a determination that the first patient identification and the second patient identification are associated with the same patient, associate the first information and the second information with the same patient identification by changing the first value associated with the first patient identification to be the second value associated with the second patient identification or by changing the second value associated with the second patient identification to be the first value associated with the first patient identification;
in response to the first patient identification and the second patient identification being associated with the same patient, detect that the first information and the second information are associated with the same encounter based at least in part on a first time period associated with the first information and a second time period associated with the second information being within a predetermined threshold; and
merge the first non-clinical information and the second non-clinical information and merge the at least partially different first and second clinical information in response to the first encounter identification and the second encounter identification being associated with the same encounter.

17. The tangible machine accessible storage device as defined in claim 16 having instructions stored thereon that, when executed, cause the machine to merge the first information and the second information when a first encounter identification of the first information and a second encounter identification of the second information are associated with the same encounter by changing a third value associated with the first encounter identification to be a fourth value associated with the second encounter identification or by changing the fourth value associated with the second encounter identification to be the third value associated with the first encounter identification.

18. The tangible machine accessible storage device as defined in claim 16 having instructions stored thereon that, when executed, cause the machine to adjust a patient billing based on identifying that the first encounter identification and the second encounter identification are associated with the same encounter.

19. The tangible machine accessible storage device as defined in claim 16 having instructions stored thereon that, when executed, cause the machine to monitor a quality of delivered care to the patient based on identifying that the first information and the second information are associated with at least one of the same patient or the same encounter.

20. The tangible machine accessible storage device as defined in claim 16 having instructions stored thereon that, when executed, cause the machine to implement a user interface capable of conveying information that is associated with the patient.

21. The tangible machine accessible storage device as defined in claim 16 having instructions stored thereon that, when executed, cause the machine to merge the at least partially different first and second clinical information by setting a merged encounter start time of the at least partially different first and second clinical information to a first encounter start time associated with the first clinical information and setting a merged encounter end time of the at least partially different first and second clinical information to a first encounter end time associated with the first clinical information, the first encounter start time being earlier than a second encounter start time associated with the second clinical information, the first encounter end time being later than a second encounter end time associated with the second clinical information, the first time period being between the first start and end times at least partially overlapping the second time period being between the second start and end times.

22. The tangible machine accessible storage device as defined in claim 16 having instructions stored thereon that, when executed, cause the machine to merge the at least partially different first and second clinical information by setting a merged encounter start time of the at least partially different first and second clinical information to a first encounter start time associated with the first clinical information and setting a merged encounter end time of the at least partially different first and second clinical information to a second encounter end time associated with the second clinical information, the first encounter start time being earlier than a second encounter start time associated with the second clinical information, the second encounter end time being later than a first encounter end time associated with the first clinical information, the first time period being between the first start and end times at least partially overlapping the second time period being between the second start and end times.

\* \* \* \* \*